United States Patent [19]

Matsukubo et al.

[11] Patent Number: 4,952,591
[45] Date of Patent: Aug. 28, 1990

[54] ANTI-ULCER UREA DERIVATIVES

[75] Inventors: Hiroshi Matsukubo, Okaya; Toyomi Matsumoto, Minowa; Mitsutomo Miyashita, Okaya; Kyuya Okamura, Ohmiya; Fukutaro Taga, Shiraoka; Haruo Sekiguchi, Ageo; Katsuhiro Hamada, Nogi, all of Japan

[73] Assignee: Kyorin Pharmaceutical Co., Ltd., Tokyo, Japan

[21] Appl. No.: 222,520

[22] Filed: Jul. 21, 1988

[30] Foreign Application Priority Data

Aug. 3, 1987 [JP] Japan ................................. 62-194060
Jul. 8, 1988 [JP] Japan ................................. 63-168887

[51] Int. Cl.$^5$ .................. A61K 31/445; C07D 211/46
[52] U.S. Cl. ..................................... 514/321; 514/327; 514/331; 514/408; 514/422; 514/424; 546/196; 546/221; 546/231; 548/526; 548/541; 548/543; 548/578
[58] Field of Search .................. 546/196, 221, 231; 548/526, 543, 541, 578; 514/321, 327, 331, 422, 424, 408

[56] References Cited

PUBLICATIONS

*Chemical Abstracts,* 103: 123484p (1985), [Ger. Offen 3,426,533, Toyofuku et al., 4/11/85].
*Chemical Abstracts,* 105: 17845p (1986), [Buschauer, A. et al., Arch. Pharm. 1986, 319 (5), 434–44].
*Chemical Abstracts,* 105: 133758m (1986), [Ger. Offen 3,438,073, Moersdorf et al., 4/24/86].

*Primary Examiner*—Richard A. Schwartz
*Attorney, Agent, or Firm*—Oblon, Spivak, McClelland, Maier & Neustadt

[57] ABSTRACT

Urea derivatives of the following formula,

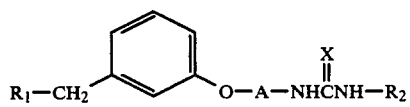

wherein $R_1$ indicates a piperidino group or pyrrolidino group which may be substituted with hydroxy group or lower alkyl group having 1 to 3 carbon atoms; A indicates an ethylene group, propylene group, butylene group or butenylene group; $R_2$ indicates a straight or branched alkyl group having 1 to 20 carbon atoms, cycloalkyl group having 3 to 6 carbon atoms, benzyl group, or phenyl group which may have 1 to 3 substituents such as lower alkyl group having 1 to 6 carbon atoms, lower alkoxy group having 1 to 3 carbon atoms, halogen atom, trifluoromethyl group, amino group, nitro group or methylenedioxy group; X indicates an oxygen or sulfur atom, the hydrates and pharmaceutically acceptable acid addition salts thereof are useful as antiulcer agents.

8 Claims, No Drawings

ANTI-ULCER UREA DERIVATIVES

DETAILED DESCRIPTION OF THE INVENTION

This invention relates to novel urea derivatives and their medically acceptable acid addition salts having a strong gastric antisecretory activity together with a strong gastric cytoprotective activity. Thus, the compounds of this invention are useful for the treatment of peptic ulcer. This invention also relates to processes for the manufacture thereof.

It has been well-known that gastric acid secretion caused by histamine is mediated by histamine $H_2$-receptor, and the blockade of this receptor by its antagonist reduces the gastric acid secretion in animals and humans (Brimblecombe, R.W., et al., J. Int. Med. Res., 3, 86–92, 1975). Several drugs of this type, such as cimetidine, are commercially available.

It has also been said that a compound which prevents or cures the gastric lesions induced by a necrotizing agent such as hydrochloric acid or absolute ethanol has gastric cytoprotective activity (Robert, A., et al., Gastroenterology, 77, 433–443. 1979). Gastric cytoprotective effect is achieved independently of the inhibitory action on gastric acid secretion. In fact, histamine $H_2$-receptor antagonists hitherto known cannot suppress the formation of gastrtic lesions induced by absolute ethanol or 0.6N HCl.

As the similar type of the compounds of the present invention, the compounds discovered by Allen & Hanburys Limited have been known (Brit. Pat. Publication No. 1,604,674 and 1,604,675). The urea derivatives mentioned in these publications, however, have only dimethylaminomethylphenoxy group, and no mention is made of piperidinomethylphenoxy group. Furthermore, these publications mentioned only histamine $H_2$-receptor antagonistic activity, but no description is made of gastric cytoprotective activity.

A number of histamine $H_2$-receptor antagonists has been developed and they bring high ulcer-healing rate in clinical therapy. However, it has come to be drawn as a serious problem that the recurrence and relapse of peptic ulcer frequently occur within weeks or a few months after withdrawal of administration of histamine $H_2$-receptor antagonist hitherto known. Recently, to improve this problem, a concomitant use of histamine $H_2$-receptor antagonist with gastric cytoprotective agent has come to be tried in practice.

In addition, it has been well-known that antiulcer drugs having gastric cytoprotective activity are more effective for gastric ulcers than for duodenal ulcers, while histamine $H_2$-receptor antagonists are more effective for duodenal ulcers than for gastric ulcers.

Therefore, it is expected that a new type of histamine $H_2$-receptor antagonist having not only strong gastric antisecretory activity but also gastric cytoprotective activity can reduce the recurrence and relapse of peptic ulcer, and also improve the healing rate and healing process of peptic ulcer.

To improve the weak points of the known histamine $H_2$-receptor antagonists, namely, to prevent the recurrence and relapse of peptic ulcer, we have continuously studied for development of the new type of histamine $H_2$-receptor antagonists. Consequently, we - have succeeded in the development of histamine $H_2$-receptor antagonists having a strong gastric antisecretory activity together with a strong gastric cytoprotective activity.

The compounds of the present invention are novel urea derivatives represented by the following formula (I).

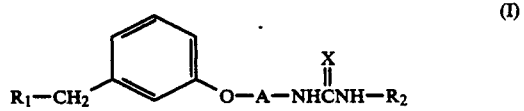

wherein $R_1$ indicates a piperidino group or pyrrolidino group which may be substituted with hydroxy group or lower alkyl group having 1 to 3 carbon atoms; A indicates an ethylene group, propylene group, butylene group or butenylene group; $R_2$ indicates a straight or branched alkyl group having 1 to 20 carbon atoms, cycloalkyl group having 3 to 6 carbon atoms, benzyl group, or phenyl group which may have 1 to 3 substituents such as lower alkyl group having 1 to 6 carbon atoms, lower alkoxy group having 1 to 3 carbon atoms, halogen atom, trifluoromethyl group, amino group, nitro group or methylenedioxy group; X indicates an oxygen or sulfur atom, the hydrates and pharmaceutically acceptable acid addition salts thereof.

According to the invention, the compounds represented by the general formula (I) are prepared through various routes as follows.

(1) The compounds represented by the general formula (I) can be prepared by allowing the compounds of the general formula (II);

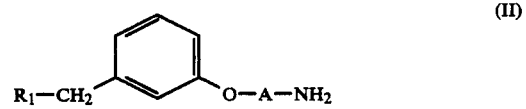

(wherein $R_1$ and $R_2$ have the same meanings as described above) to react with isocyanate derivatives represented by the general formula (III).

(wherein $R_2$ and X have the same meanings as described above) Typically, they can be prepared by allowing isocyanate derivatives (III) to react with compounds of the general formula (II) in a suitable solvent, for example, alcohol, benzene, chloroform, dichloromethane, and so on. The reaction temperature is selected appropriately within a range of room temperature to boiling point of the solvents. At this time, the addition of a catalyst, such as triethylamine, is also preferable.

(2) The compounds represented by the general formula (Ia);

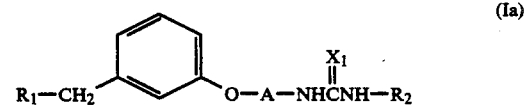

(wherein $X_1$ indicates an oxygen atom and $R_1$, $R_2$ and A have the same meanings as described above) can be prepared by allowing the compounds represented by the general formula (IV)

(wherein $R_2$ has the same meaning as described above) to react with compounds of the general formula (II) in the presence of N,N'-carbonyldiimidazole. Typically, they can be prepared by the direct reaction of amines represented by the general formula (IV) with imidazolecarbonylamides, which are obtained from amines with N,N'-carbonyldiimidazole. They can be also prepared by the direct reaction of amines represented by the general formula (II) with imidazolecarbonyl amides, which are obtained from amines (IV) with N,N'-carbonyldiimidazole. There is no different either case of isolation and non-isolation of imidazolecarbonylamides. The suitable solvent of this reaction is organic solvent such as benzene, tetrahydrofuran (THF), chloroform, dichloromethane, and so on. The reaction temperature is selected appropriately within a range of room temperature to boiling point of the solvents.

(3) The compounds represented by the general formula (Ia) can be prepared by allowing the compounds of the general formula (II) to react with the compounds of the general formula (V);

$$Y_1COOY_2 \qquad (V)$$

(wherein $Y_1$ and $Y_2$ indicate a leaving group each independently) and the compounds of the general formula (IV). They can be prepared by the reaction that compounds of a general formula (II) are at first converted to its urethanes in the presence of the compound of the general formula (V) and the urethanes are reacted with compounds of the general formula (IV). They can be also prepared by the reaction that compounds of the general formula (IV) are at first converted to its urethanes in the presence of the compound of the general formula (V) and the urethanes are reacted with compounds of the general formula (II). There is no different in either case of isolation and non-isolation of urethanes. The suitable solvent of this reaction is organic solvent such as benzene, THF, chloroform, dichloromethane, dimethylformamide (DMF), and so on. The reaction temperature is selected appropriately within a range of room temperature to boiling point of the solvents. At this time, the addition of the catalysts such as pyridine, triethylamine, and so on, is also preferable. In this case, it is desirable that leaving group $Y_1$ of the compound represented by the general formula (V) is halogen atom for example, chlorine or bromine atom and leaving group $Y_2$ is lower alkyl group.

(4) The compounds represented by the general formula (I) can be prepared by allowing phenol derivatives represented by the general formula (VI);

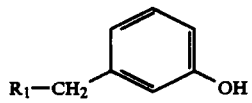

(VI)

(wherein $R_1$ has the same meaning as described above) to react with compounds represented by the general formula (VII).

(VII)

(wherein $Y_3$ indicates a leaving group and $R_2$, A and X have the same meanings as described above). The suitable solvent of this reaction is organic solvent such as methanol, ethanol, propanol, isopropanol, 3-methoxypropanol, and so on. The reaction temperature is selected appropriately within a range of 0° C. to boiling point of the solvents. At this time, the addition of the catalysts such as basic catalyst, for example, sodium, sodium hydroxide, potassium hydroxide, sodium bicarbonate, sodium carbonate, and so on, is also preferable. In this case, it is also desirable that leaving group $Y_1$ of the compound represented by the general formula (VII) is halogen atom for example, chlorine or bromine atom.

(5) The compounds represented by the general formula (I) can be prepared by allowing the compounds represented by the general formula (VIII)

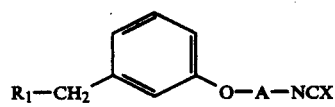

(VIII)

(wherein $R_1$, A and X have the same meanings as described above) to react with the compounds represented by the general formula (IV). The suitable solvent of this reaction is organic solvent such as ethanol, benzene, chloroform, dichloromethane, THF, DMF, and so on. The reaction temperature is selected appropriately within a range of room temperature to boiling point of the solvents At this time, the addition of the catalyst, such as triethylamine, and so on, is also preferable.

(6) The compounds represented by the general formula (Ic);

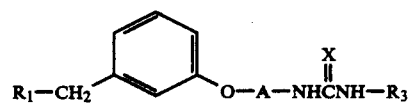

(Ic)

(wherein $R_3$ indicates an aminophenyl group and $R_1$, A and X have the same meanings as described above) can be prepared by hydrogenation of the compounds represented by the general formula (Ib).

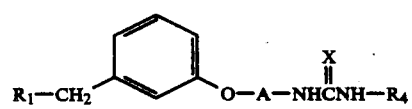

(Ib)

(wherein $R_4$ indicates a nitrophenyl group and $R_1$, A and X have the same meanings as described above) This reduction is accomplished by the reaction with metal such as, for example, iron, tin, and so on, in the presence of acid, such as, hydrochloric acid, acetic acid, and so on, in the suitable organic solvent, such as, ethanol, isopropanol, dioxane, and so on. The reaction temperature is selected appropriately within a range of room temperature to boiling point of the solvents This reduction is also accomplished by the catalytic hydrogenation using palladium on charcoal, and so on, in the inert solvent such as, ethanol, isopropanol, 3-methoxybutanol, dioxane, DMF, and so on. The temperature is selected appropriately within a range of room temperature to boiling point of the solvents.

Furthermore, the compounds represented by the formula (I) can be converted to the medically acceptable acid addition salts by treatment with acid as usual manner. The acid may be inorganic acid such as, hydrochloric acid, hydrobromic acid, sulfuric acid, phosphoric acid, and so on, or organic acid such as, acetic acid, propionic acid, citric acid, lactic acid, maleic acid, fumaric acid, succinic acid, tartaric acid, methanesulfonic acid, and so on.

The following examples will further illustrate the present invention without, however, limiting it thereto.

EXAMPLE 1

N-(4-Methoxyphenyl)-N'-[3-(3-piperidinomethylphenoxy)propyl]urea

To the mixture of 3-(3-piperidinomethylphenoxy)-propylamine (3.1 g) in ethanol (31 ml) was added 4-methoxyphenylisocyanate (1.9 g) dropwise slowly under cooling on an ice-water bath. The reaction mixture was stirred at room temperature for 2.5 hours and then concentrated under reduced pressure. The resulting residue was dissolved in dichloromethane (50 ml), washed with diluted hydrochloric acid, saturated aqueous sodium bicarbonate solution and saturated aqueous sodium chloride solution successively and dried over anhydrous magnesium sulfate. After removal of the solvent under reduced pressure, the crude product (3.3 g) was obtained (yield 66.0 %). This crude product was recrystallized from ethanol to give the title compound (2.1 g), mp 111°–112° C.

Analysis (%) for $C_{23}H_{31}N_3O_3$, Calcd. (Found): C, 69.49 (69.28); H, 7.86 (7.86); N, 10.57 (10.54).

EXAMPLE 2–50

The analytical data of the compounds of Example 2–50, synthesized as same manner as the process of Example 1, are summarized in Table 1 (1) to (4).

TABLE 1

| Ex. No. | $R_1$ | A | X | $R_2$ | mp (°C.) | Molecular formula | Analysis (%) Calcd. Found C H N |
|---|---|---|---|---|---|---|---|
| 2 | piperidino-N— | —CH₂CH₂CH₂— | O | phenyl | 109–111 | $C_{22}H_{29}N_3O_2$ | 71.90  7.95  11.43<br>71.94  8.00  11.39 |
| 3 | piperidino-N— | —CH₂CH₂CH₂— | O | 4-CH₃-phenyl | 103–105 | $C_{23}H_{31}N_3O_2$ | 72.41  8.19  11.01<br>72.31  8.15  10.92 |
| 4 | piperidino-N— | —CH₂CH₂CH₂— | O | 4-CF₃-phenyl | 114–116 | $C_{23}H_{28}F_3N_3O_2$ | 63.43  6.48  9.65<br>63.41  6.50  9.58 |
| 5 | piperidino-N— | —CH₂CH₂CH₂— | O | 3-CF₃-phenyl | oily | $C_{23}H_{28}F_3N_3O_2$ | Mass: 435 (M⁺) |
| 6 | piperidino-N— | —CH₂CH₂CH₂— | O | 4-Cl-phenyl | 131–133 | $C_{22}H_{28}ClN_3O_2$ | 65.74  7.02  10.45<br>65.76  6.94  10.49 |
| 7 | piperidino-N— | —CH₂CH₂CH₂— | O | 3-Cl-phenyl | 58–61 | $C_{22}H_{28}ClN_3O_2$ | Mass: 402 (M⁺) |
| 8 | piperidino-N— | —CH₂CH₂CH₂— | O | —CH₂CH₂CH₃ | 99–101 | $C_{19}H_{31}N_3O_2$ | 68.43  9.37  12.60<br>68.40  9.38  12.61 |
| 9 | piperidino-N— | —CH₂CH₂CH₂— | O | —CH₂-phenyl | 109–112 | $C_{23}H_{31}N_3O_2$ | 72.41  8.19  11.01<br>72.47  8.18  10.98 |
| 10 | piperidino-N— | —CH₂CH₂CH₂— | O | 2-OCH₃-phenyl | 92–94 | $C_{23}H_{31}N_3O_3$ | 69.49  7.86  10.57<br>69.61  7.87  10.54 |

TABLE 1-continued

| Ex. No. | R₁ | A | X | R₂ | mp (°C.) | Molecular formula | Analysis (%) Calcd. / Found C  H  N |
|---|---|---|---|---|---|---|---|
| 11 | piperidino | $-CH_2CH_2CH_2-$ | O | 2,5-dimethoxyphenyl | 80–83 | $C_{24}H_{33}N_3O_4$ | 67.42 7.78 9.83 / 67.34 7.74 9.83 |
| 12 | piperidino | $-CH_2CH_2CH_2-$ | O | 2,5-dimethoxyphenyl (isomer) | 95–98 | $C_{24}H_{33}N_3O_4$ | 67.42 7.78 9.83 / 67.28 7.73 9.81 |
| 13 | piperidino | $-CH_2CH_2CH_2-$ | O | 3-methoxyphenyl | 114–118 | $C_{23}H_{31}N_3O_3 \cdot HCl \cdot H_2O$ | 61.12 7.58 9.30 / 61.33 7.36 9.30 |
| 14 | piperidino | $-CH_2CH_2CH_2-$ | O | 3-nitrophenyl | 64–66 | $C_{22}H_{28}N_4O_4$ | Mass: 412 (M⁺) |
| 15 | piperidino | $-CH_2CH_2CH_2-$ | O | 4-nitrophenyl | Oily | $C_{22}H_{28}N_4O_4 \cdot \tfrac{1}{4} H_2O$ | 62.69 6.93 13.29 / 62.89 6.81 13.31 |
| 16 | piperidino | $-CH_2CH_2CH_2-$ | O | $-CH_2CH_3$ | 80–81.5 | $C_{18}H_{29}N_3O_2$ | 67.68 9.15 13.15 / 67.61 9.13 13.12 |
| 17 | piperidino | $-CH_2CH_2CH_2-$ | O | $-CH_2CH_2CH_3$ | 88–91 | $C_{20}H_{33}N_3O_2$ | 69.13 9.57 12.09 / 69.18 9.57 12.12 |
| 18 | piperidino | $-CH_2CH_2CH_2-$ | O | $-(CH_2)_{17}CH_3$ | 100–102 | $C_{34}H_{61}N_3O_2$ | 75.09 11.13 7.73 / 75.19 11.33 7.75 |
| 19 | piperidino | $-CH_2CH_2CH_2-$ | O | cyclohexyl | 94–96 | $C_{22}H_{35}N_3O_2$ | 70.74 9.44 11.25 / 70.91 9.45 11.30 |
| 20 | piperidino | $-CH_2CH_2CH_2-$ | S | 4-methoxyphenyl | 114–116 | $C_{23}H_{31}N_3O_2S$ | 66.80 7.56 10.16 / 66.60 7.60 10.05 |
| 21 | piperidino | $-CH_2CH_2CH_2-$ | O | $-CH_3$ | 73–75 | $C_{17}H_{27}N_3O_2$ | 66.85 8.91 13.76 / 66.81 8.82 13.69 |

TABLE 1-continued

| Ex. No. | R₁ | A | X | R₂ | mp (°C.) | Molecular formula | Analysis (%) C H N | Calcd. Found N |
|---|---|---|---|---|---|---|---|---|
| 22 | 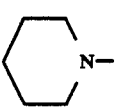 | —CH₂CH₂CH₂— | O | —C(CH₃)₃ | 94–95 | C₂₀H₃₃N₃O₂ | 69.13 9.57<br>69.24 9.59 | 12.09<br>12.12 |
| 23 | 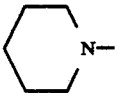 | —CH₂CH₂CH₂— | S | —CH₂CH₂CH₃ | 126–130 | C₁₉H₃₁N₃OS<br>HCl | 59.12 8.36<br>59.14 8.35 | 10.89<br>10.93 |
| 24 | 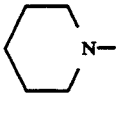 | —CH₂CH₂CH₂— | S | —CH₂CHCH₃<br>          \|<br>          CH₃ | 69–71 | C₂₀H₃₃N₃OS | 66.07 9.15<br>66.13 9.15 | 11.56<br>11.57 |
| 25 | 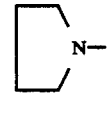 | —(CH₂)₄— | O | 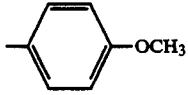 | 90–91 | C₂₃H₃₁N₃O₂ | Mass: 397 (M⁺) | |
| 26 | 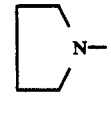 | —(CH₂)₄— | O | —CH₂CH₂CH₃ | 73–74.5 | C₁₉H₃₁N₃O₂ | 68.43 9.37<br>68.05 9.30 | 12.60<br>12.56 |
| 27 | 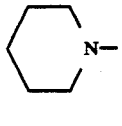 | —CH₂CH₂CH₂— | S | 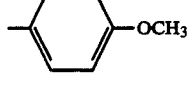 | 107–108 | C₂₃H₃₁N₃OS | 66.80 7.56<br>66.60 7.60 | 10.16<br>10.05 |
| 28 | 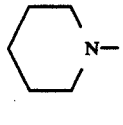 | —CH₂CH=CHCH₂—<br>trans | O | —CH₃ | 91–94 | C₁₈H₂₇N₃O₂ | 68.11 8.57<br>67.83 8.70 | 13.24<br>13.07 |
| 29 | 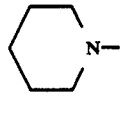 | —CH₂CH=CHCH₂—<br>cis | O | —CH₃ | 65–67 | C₁₈H₂₇N₃O₂ | 68.11 8.57<br>68.09 8.66 | 13.24<br>13.20 |
| 30 | 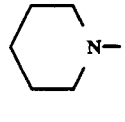 | —CH₂CH=CHCH₂—<br>trans | O | —CH₂CH₃ | 66–69 | C₁₉H₂₉N₃O₂ | 68.85 8.82<br>68.45 8.92 | 12.68<br>12.40 |
| 31 | 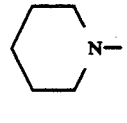 | —CH₂CH=CHCH₂—<br>cis | O | —CH₂CH₃ | 72–74 | C₁₉H₂₉N₃O₂ | 68.85 8.82<br>68.85 8.88 | 12.68<br>12.62 |
| 32 | 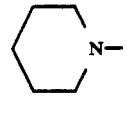 | —CH₂CH=CHCH₂—<br>trans | O | —CH₂CH₂CH₃ | 87–89 | C₂₀H₃₁N₃O₂ | 69.53 9.04<br>69.70 9.10 | 12.16<br>12.17 |
| 33 | 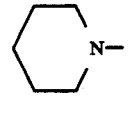 | —CH₂CH=CHCH₂—<br>cis | O | —CH₂CH₂CH₃ | 70–73 | C₂₀H₃₁N₃O₂ | Mass: 345 (M⁺) | |
| 34 | 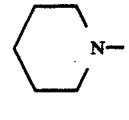 | —CH₂CH=CHCH₂—<br>trans | O | —C(CH₃)₃ | 100–102 | C₂₁H₃₃N₃O₂ | 70.16 9.25<br>70.23 9.15 | 11.69<br>11.70 |

TABLE 1-continued

| Ex. No. | R₁ | A | X | R₂ | mp (°C.) | Molecular formula | Analysis (%) C | H | Calcd. Found N |
|---|---|---|---|---|---|---|---|---|---|
| 35 | piperidin-N- | —CH₂CH=CHCH₂— trans | O | 4-methoxyphenyl | 101–103 | $C_{24}H_{31}N_3O_3$ | 70.39 70.11 | 7.63 7.61 | 10.26 10.23 |
| 36 | piperidin-N- | —CH₂CH=CHCH₂— cis | O | 4-methoxyphenyl | 88–90 | $C_{24}H_{31}N_3O_3$ | 70.39 70.44 | 7.63 7.67 | 10.26 10.23 |
| 37 | 4-hydroxypiperidin-N- | —CH₂CH₂CH₂— | O | —CH₃ | 106–108 | $C_{17}H_{27}N_3O_3$ | 63.53 63.47 | 8.47 8.49 | 13.07 13.00 |
| 38 | 4-methylpiperidin-N- | —CH₂CH₂CH₂— | O | —CH₃ | 73–76 | $C_{18}H_{29}N_3O_2$ | Mass: 319 (M⁺) | | |
| 39 | 4-hydroxypiperidin-N- | —CH₂CH₂CH₂— | O | —CH(CH₃)₂ | 114–117 | $C_{19}H_{31}N_3O_3$ | 65.30 65.27 | 8.94 8.94 | 12.02 12.07 |
| 40 | 4-methylpiperidin-N- | —CH₂CH₂CH₂— | O | —CH(CH₃)₂ | 92–95 | $C_{20}H_{33}N_3O_2$ | Mass: 347 (M⁺) | | |
| 41 | 4-methylpiperidin-N- | —CH₂CH₂CH₂— | O | —CH₂CH₂CH₃ | 83–85 | $C_{20}H_{33}N_3O_2$ | Mass: 347 (M⁺) | | |
| 42 | 4-methylpiperidin-N- | —CH₂CH₂CH₂— | O | —CH₂CH₃ | 61–64 | $C_{19}H_{31}N_3O_2$ | Mass: 333 (M⁺) | | |
| 43 | 4-hydroxypiperidin-N- | —CH₂CH₂CH₂— | O | —CH₂CH₃ | 81–83 | $C_{18}H_{29}N_3O_3$ | Mass: 335 (M⁺) | | |
| 44 | 4-hydroxypiperidin-N- | —CH₂CH₂CH₂— | O | 4-methoxyphenyl | 126–128 | $C_{23}H_{31}N_3O_4$ | 66.81 66.79 | 7.56 7.58 | 10.16 10.10 |
| 45 | piperidin-N- | —(CH₂)₄— | O | —CH₂CH₃ | 57–58 | $C_{19}H_{31}N_3O_2$ | Mass: 333 (M⁺) | | |
| 46 | piperidin-N- | —(CH₂)₄— | O | —CH₂CH₂CH₃ | 87–88 | $C_{20}H_{33}N_3O_2$ | Mass: 347 (M⁺) | | |
| 47 | piperidin-N- | —(CH₂)₄— | O | —CH(CH₃)₂ | 54–57 | $C_{20}H_{33}N_3O_2$ | Mass: 347 (M⁺) | | |

TABLE 1-continued

| Ex. No. | $R_1$ | A | X | $R_2$ | mp (°C.) | Molecular formula | Analysis (%) Found C H N | Calcd. |
|---|---|---|---|---|---|---|---|---|
| 48 | piperidino-N— | —$(CH_2)_4$— | O | —$CH_3$ | 52–53.5 | $C_{18}H_{29}N_3O_2$ | Mass: 319 (M+) | |
| 49 | piperidino-N— | —$(CH_2)_2$— | O | —$CH_2CH_3$ | oily | $C_{17}H_{27}N_3O_2$ | Mass: 305 (M+) | |
| 50 | piperidino-N— | —$(CH_2)_2$— | O | —$CH_2CH_2CH_3$ | 65–66 | $C_{18}H_{29}N_3O_2$ | Mass: 319 (M+) | |

EXAMPLE 51

N-(4-Ethoxyphenyl)-N'-[3-(3-piperidinomethylphenoxy)propyl]urea (1) To the mixture of 4-phenetidine (4.6 g) and triethylamine (3.4 g) in dichloromethane (46 ml) was added ethyl chlorocarbonate (3.6 g) dropwise under cooling on an ice-water bath and the reaction mixture was stirred at room temperature for an hour. The reaction mixture was washed with water, dried over anhydrous magnesium sulfate and concentrated under reduced pressure. The resulting precipitate was suspended in petroleum ether and collected by filtration to give ethyl N-(4-ethoxyphenylcarbamate (4.0 g; yield 56.9 %), mp 90°–92 ° C.

(2) The mixture of 3-(3-piperidinomethylphenoxy)-propylamine (4.7 g) and ethyl N-(4-ethoxyphenyl)carbamate (4.0 g) in 3-methoxy-2-butanol (20 ml) was refluxed for 6 hours and then concentrated under reduced pressure The resulting residue was dissolved in dichloromethane, washed with water, diluted hydrochloric acid solution, saturated aqueous sodium bicarbonate solution and saturated aqueous sodium chloride solution successively and dried over magnesium sulfate. After removal of the solvent under reduced pressure, the resulting residue was purified by silica gel flash column chromatography to give the precipitate (0.9 g; yield 11.4 %). This precipitate was recrystallized from ethanol to give the title compound (0.5 g), mp 109°–111 ° C.

Analysis (%) for $C_{24}H_{33}N_3O_3$, Calcd. (Found): C, 70.04 (70.18); H, 8.08 (8.06); N, 10.21 (10.20).

EXAMPLE 52

N-(3,4-Methylenedioxyphenyl)-N'-[3-(3-piperidinomethylphenoxy)propyl]urea

To the solution of N,N'-carbonyldiimidazole (4.0 g) in dichloromethane (60 ml) was added the solution of 3,4-methylenedioxyaniline (3.4 g) in dichloromethane (20 ml) dropwise at 0°–5° C. The mixture was stirred at the same temperature for an hour and then stirred at room temperature for an hour. To the mixture was further added the solution of 3-(3-piperidinomethylphenoxy)propylamine (6.1 g) in dichloromethane (30 ml) at 0 ° C. The reaction mixture was stirred at the same temperature for an hour and then stirred at room temperature for an hour. To the reaction mixture was added water (60 ml). The organic layer was separated and dried over anhydrous magnesium sulfate. After removal of the solvent under reduced pressure, the resulting residue was suspended in ether and collected by filtration to give the crude product (6.7 g; yield 67.0 %). This product was recrystallized from ethanol to give the title compound (5.0 g), mp 128°–130 ° C.

Analysis (%) for $C_{23}H_{29}N_3O_4$, Calcd. (Found): C, 67.13 (67.13); H, 7.10 (7.08); N, 10.21 (10.17).

EXAMPLE 53–60

The analytical data of the compounds of Example 53–60, synthesized as same manner as the process of Example 52, are summarized in Table 2.

TABLE 2

| Ex. No. | $R_1$ | A | X | $R_2$ | mp (°C.) | Molecular formula | Analysis (%) C H N | Calcd. Found |
|---|---|---|---|---|---|---|---|---|
| 53 | piperidino-N— | —$CH_2CH_2CH_2$— | O | —C$_6$H$_4$—OEt | 109–111 | $C_{24}H_{33}N_3O_3$ | 70.04 8.08 10.21 / 70.02 8.08 10.21 | |
| 54 | piperidino-N— | —$CH_2CH_2CH_2$— | O | —$CH(CH_3)_2$ | 93–95 | $C_{19}H_{31}N_3O_2$ | 68.43 9.37 12.60 / 68.38 9.37 12.60 | |

TABLE 2-continued

| Ex. No. | R$_1$ | A | X | R$_2$ | mp (°C.) | Molecular formula | Analysis (%) Found C H N | Calcd. C H N |
|---|---|---|---|---|---|---|---|---|
| 55 | piperidino-N— | —CH$_2$CH$_2$CH$_2$— | O | —CH(CH$_3$)CH$_2$CH$_3$ | 68–71 | C$_{20}$H$_{33}$N$_3$O$_2$·HCl | Mass: 347 (M$^+$) | |
| 56 | piperidino-N— | —CH$_2$CH$_2$CH$_2$— | O | —CH$_2$CH(CH$_3$)CH$_3$ | 68–71 | C$_{20}$H$_{33}$N$_3$O$_2$ | Mass: 347 (M$^+$) | |
| 57 | piperidino-N— | —CH$_2$CH$_2$CH$_2$— | O | cyclopropyl | 75–77 | C$_{19}$H$_{29}$N$_3$O$_2$ | Mass: 331 (M$^+$) | |
| 58 | piperidino-N— | —CH$_2$CH=CHCH$_2$— trans | O | —CH(CH$_3$)$_2$ | 84–86 | C$_{20}$H$_{31}$N$_3$O$_2$ | 69.53 9.04 12.16 | 69.34 9.11 12.15 |
| 59 | piperidino-N— | —CH$_2$CH=CHCH$_2$— trans | O | cyclopropyl | 75–77 | C$_{20}$H$_{29}$N$_3$O$_2$ | 69.94 8.51 12.33 | 69.82 8.63 12.19 |
| 60 | piperidino-N— | —CH$_2$CH=CHCH$_2$— trans | O | 4-OEt-phenyl | 117–119 | C$_{25}$H$_{33}$N$_3$O$_3$ | 70.89 7.85 9.92 | 70.65 7.77 9.82 |

EXAMPLE 61

N-(3-Aminophenyl)-N'-[3-(3-piperidinomethylphenoxy)propyl]urea

To the mixture of N-(3-nitrophenyl)-N'-[3-(3-piperidinomethylphenoxy)propyl]urea (4.6 g) in ethanol (46 ml) was added tin (2.6 g). To the reaction mixture was added concentrated hydrochloric acid (1.9 ml) at room temperature under stirring, further added concentrated hydrochloric acid (18.2 ml) under heating on a water bath. The reaction mixture was refluxed for 6 hours, concentrated under reduced pressure, diluted with water (100 ml), alkalized with aqueous sodium hydroxide solution and extracted with dichloromethane (200 ml). The organic layer was washed with saturated aqueous sodium chloride solution, dried over anhydrous magnesium sulfate and concentrated under reduced pressure to give the crude precipitate (3.8 g; yield 88.4 %). This precipitate was recrystallized two times from ethanol to give the title compound (1.8 g), mp 116°–118 ° C. Analysis (%) for C$_{22}$H$_{30}$N$_4$O$_2$, Calcd. (Found): C, 69.08 (68.91); H, 7.91 (7.90); N, 14.65 (14.54).

EXAMPLE 62

N-Methyl-N'-[3-(3-piperidinomethylphenoxy)propyl]urea

To DMF (10 ml) was added sodium hydride (0.7 g; 60 % in oil) portionwise under cooling, further added the mixture of 3-piperidinophenol (3.3 g) in DMF (7 ml) dropwise and stirred at room temperature for an hour. To the reaction mixture was added N-(3-chloropropyl)-N'-methylurea (2.6 g) at room temperature and stirred for 3 hours at the same temperature. The reaction mixture was poured into water and extracted with dichloromethane. The organic layer was dried over anhydrous magnesium sulfate and concentrated under reduced pressure. The resulting residue was suspended in petroleum ether and collected by filtration to give the crude precipitate (2.8 g, yield 52.8 %). This precipitate was recrystallized from ethyl acetate to give the title compound (0.5 g).

Thus obtained compound was identified with the compound described in example 21 by comparison of analytical data.

EXAMPLE 63

The analytical data of the compound of Example 63, synthesized as same manner as the process of Example 62, is summarized in Table 3.

TABLE 3

| Ex. No. | $R_1$ | A | X | $R_2$ | mp (°C.) | Molecular formula | Analysis (%) C H N | Calcd. Found |
|---|---|---|---|---|---|---|---|---|
| 63 | HO—⟨piperidine⟩—N— | —CH$_2$CH$_2$CH$_2$— | O | —⟨phenyl⟩—OEt | 142–144 | $C_{24}H_{33}N_3O_4$ | 67.42 7.78 9.83 / 67.23 7.86 9.74 | |

EXAMPLE 64

N-Ethyl-N'-[3-(3-piperidinomethylphenoxy)propyl]urea

To DMF (5 ml) was added sodium hydride (0.5 g; 60 % in oil) portionwise under cooling, further added the mixture of 3-piperidinophenol (2.3 g) in DMF (7 ml) dropwise and stirred at room temperature for an hour. To the reaction mixture was added N-(3-chloropropyl)-N'-methylurea (2.0 g) at room temperature, stirred for 3 hours at the same temperature and allowed to stand for overnight. The reaction mixture was poured into icewater and extracted with dichloromethane. The organic layer was dried over anhydrous magnesium sulfate and concentrated under reduced pressure. The resulting residue was crystallized from petroleum ether, collected by filtration to give the title compound (0.6 g). The filtrate was concentrated and purified by silica gel column chromatography (eluting with acetone) to give the further title compound (0.8 g).

Thus obtained compound was identified with the compound described in example 16 by comparison of analytical data.

The compounds of this invention are histamine $H_2$-receptor antagonists with both strong gastric antisecretory and gastric cytoprotection as shown by following experiments.

EXPERIMENT 1

Gastric antisecretion

Male Donryu rats, weighing about 200 g, were fasted for 24 hours before the experiment. Under urethane anesthesia (1.25 g/kg,i.p.), the abdomen was incised and the pylorus was ligated. The gastric cannula was implanted in the forestomach (Acute fistula method). Gastric secretion from cannula was collected into test tubes every one hour and the acid output was titrated. Histamine (10 mg/kg) was intramuscularly given after the first collection of gastric juice. Drugs were intraduodenally given after the second collection of the gastric juice. The results are shown in Table 4.

TABLE 4

| Example | Dose (mg/kg, i.d.) | Inhibition (%) |
|---|---|---|
| 1 | 12.5 | 70.7 |
|   | 25 | 98.5 |
| 8 | 1 | 49.5 |
|   | 3 | 77.5 |
|   | 6 | 81.3 |
| 16 | 5 | 49.5 |
|   | 10 | 77.2 |
| 29 | 3 | 39.1 |
|   | 5 | 80.8 |
| 51 | 1 | 29.0 |
|   | 6 | 52.7 |
|   | 25 | 97.1 |
| 54 | 2 | 16.1 |
|   | 5 | 68.2 |
|   | 10 | 78.8 |
| Cimetidine | 12.5 | 51.9 |

TABLE 4-continued

| Example | Dose (mg/kg, i.d.) | Inhibition (%) |
|---|---|---|
|  | 25 | 80.0 |
|  | 50 | 100.0 |

EXPERIMENT 2

Histamine $H_2$-receptor antagonism

Male Hartley guinea-pigs, weighing between 300 and 400 g, were used in the experiment. The right atrium was dissected and suspended at 0.5 g tension in a 10 ml organ bath containing Krebs-Henseleit's solution, kept at 32±1° C. and bubbled with the gas mixture (95 % $O_2$ and 5 % $CO_2$). Contractions were recorded with a force-displacement transducer through a strain gange. Cumulative concentration-response curves for the positive chronotropic effect of histamine on atrium were displaced to the right in parallel by drugs, and the effects of test drugs were calculated as the $pA_2$ values. Drugs were added into the organ bath 5 minutes before histamine treatment. The results are shown in Table 5.

TABLE 5

| Example | $pA_2$ |
|---|---|
| 1 | 6.58 |
| 8 | 7.38 |
| 16 | 7.18 |
| 29 | 7.45 |
| 51 | 6.60 |
| 54 | 7.56 |
| Cimetidine | 6.58 |

EXPERIMENT 3

Gastric cytoprotection (0.6 N HCl-induced gastric lesions)

Male Donryu rats, weighing about 200 g, were deprived of food and water for 24 hours. One ml of 0.6N HCl solution was given orally and the animals were killed an hour later. The stomach of each animal was removed and fixed 0.5 % neutral formalin solution according to the method of Brodie and Hanson (Gastroenterology 38, 353–360, 1960). The length (mm) of each gastric lesion was measured under a dissecting microscope, summed, and used as an index for evaluation. Drugs were orally given an hour before 0.6 N HCl solution treatment. The results are shown in Table 6.

TABLE 6

| Example | Dose (mg/kg, p.o.) | Inhibition (%) |
|---|---|---|
| 1 | 25 | 30.1 |
|   | 50 | 45.1 |
|   | 100 | 67.4 |
| 8 | 1 | 26.4 |
|   | 6 | 55.4 |
|   | 16 | 67.4 |
| 16 | 6 | 52.6 |

TABLE 6-continued

| Example | Dose (mg/kg, p.o.) | Inhibition (%) |
| --- | --- | --- |
| | 25 | 78.0 |
| | 50 | 89.4 |
| 29 | 5 | 49.3 |
| | 25 | 73.8 |
| 51 | 50 | 63.4 |
| 54 | 6 | 36.1 |
| | 25 | 73.0 |
| | 50 | 70.1 |
| Cimetidine | 100 | 22.0 |

These data suggest that the compounds of this invention are histamine $H_2$-receptor antagonists with both strong gastric antisecretion and gastric cytoprotection. Furthermore, their gastric antisecretion were more potent than that of cimetidine. That is, the compounds of this invention may process more potent antiulcer activity for the treatment of peptic ulcer in clinical therapy.

What is claimed is:

1. A urea compound of the formula (I):

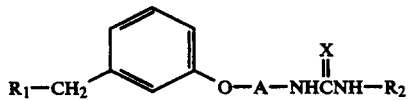

wherein $R_1$ indicates a piperidino group or pyrrolidino group which may be substituted with a hydroxy group or a lower alkyl group having 1 to 3 carbon atoms; A indicates an ethylene, propylene, butylene or butenylene group; $R_2$ indicates a cycloalkyl group having 3 to 6 carbon atoms, a benzyl group, or a phenyl group which may have 1 to 3 substitutents selected from the group consisting of lower alkyl having 1 to 3 carbon atoms, lower alkoxy having 1 to 3 carbon atoms, halogen, trifluoromethyl, amino, nitro or methylenedioxy; X indicates oxygen, or the hydrate or a pharmaceutically acceptable acid addition salt thereof.

2. The compound as claimed in claim 1, wherein $R_1$ indicates a piperidino group.

3. The compound as claimed in claim 1, wherein $R_1$ indicates a 4-methylpiperidino group.

4. The compound as claimed in claim 1, wherein $R_1$ indicates a 4-hydroxypiperidino group.

5. The compound as claimed in claim 1, wherein $R_2$ indicates a straight or branched lower alkyl group having 1 to 6 carbon atoms.

6. The compound as claimed in claim 1, wherein $R_2$ indicates a cycloalkyl group having 3 to 6 carbon atoms.

7. The compound as claimed in claim 1, wherein A indicates a propylene or butenylene group.

8. An anti-ulcer pharmaceutical composition containing a therapeutically effective amount of a compound of formula (I):

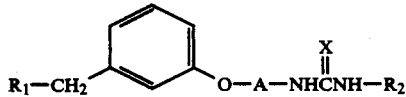

wherein $R_1$ indicates a piperidino group or a pyrrolidino group which may be substituted with a hydroxy group or a lower alkyl group having 1 to 3 carbon atoms; A indicates an ethylene, propylene, butylene or a butyenylene group; $R_2$ indicates a cycloalkyl group having 3 to 6 carbon atoms, a benzyl group, or a phenyl group which may have 1 to 3 substituents selected from the group consisting of lower alkyl having 1 to 3 carbon atoms, lower alkoxy having 1 to 3 carbon atoms, halogen, trifluoromethyl, amino, nitro or methylenedioxy; X is oxygen, the hydrate or a pharmaceutically acceptable acid addition salt thereof; and an inert pharmaceutically acceptable carrier.

* * * * *